(12) United States Patent
Takami

(10) Patent No.: US 6,348,035 B1
(45) Date of Patent: Feb. 19, 2002

(54) CONNECTION SYSTEM FOR ELECTRONIC ENDOSCOPE

(75) Inventor: Satoshi Takami, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/391,348

(22) Filed: Sep. 8, 1999

(30) Foreign Application Priority Data

Sep. 9, 1998 (JP) .......................................... 10-254987
Sep. 9, 1998 (JP) .......................................... 10-255024

(51) Int. Cl.[7] .................................................. A61B 1/00
(52) U.S. Cl. ......................... 600/132; 600/110; 348/75; 200/51 R; 200/51.09; 200/51.1; 439/188; 439/315
(58) Field of Search ................................. 600/109, 110, 600/117, 118, 132; 348/65, 75; 200/18, 51 R, 51.09, 51.1; 439/188, 315, 924.1

(56) References Cited

U.S. PATENT DOCUMENTS

| 4,346,419 A | * | 8/1982 | Janniello ................. 200/51.09 |
| 4,860,094 A | | 8/1989 | Hibino et al. |
| 5,951,462 A | * | 9/1999 | Yamanaka .................. 600/118 |
| 6,184,922 B1 | * | 2/2001 | Saito et al. ................... 348/75 |

FOREIGN PATENT DOCUMENTS

| JP | 2503005 | 3/1996 | |
| JP | 9-192088 | 7/1997 | |
| JP | 10-165404 A | * 6/1998 | ............ A61B/1/00 |

* cited by examiner

*Primary Examiner*—John Mulcahy
(74) *Attorney, Agent, or Firm*—Greenblum & Bernstein, P.L.C.

(57) ABSTRACT

A connection system for an electronic endoscope, including a flexible scope and a video-signal processing unit, is utilized to establish a detachable connection between the scope and the unit. The scope has a solid image sensor to produce image-pixel signals, and the unit has a processor for processing the image-pixel signals to produce a video signal. The scope includes a first power line, a first group of signal lines and a first ground line which are utilized to feed said image-pixel signals to the unit, and the unit include a second power line, a second group of signal lines and a second ground line which are utilized to receive the image-pixel signals from the scope. A transistor is provided in one of the first and second power lines, and is usually in an OFF-state. The OFF-state of the transistor is changed to an ON-state after the respective connections are completely established between the first power line, first group of signal lines and first ground line and the second power line, second group of signal lines and second ground line.

16 Claims, 13 Drawing Sheets

CONNECTION SYSTEM FOR ELECTRONIC ENDOSCOPE

BACKGROUND OF THE INVENTION

1. Field of the Invention

The present invention generally relates to an electronic endoscope comprising a flexible conduit or scope and a video-signal processing unit to which the flexible scope is detachably connected at a proximal end thereof, and more particularly relates to a connection system for establishing a connection between the flexible scope and the video-signal processing unit.

2. Description of the Related Art

In such an electronic endoscope, the flexible scope includes an objective lens system provided at the distal end thereof, and a solid-state image sensor, such as a CCD (charge-coupled-device) image sensor, associated therewith. The flexible scope also includes an optical light guide extended therethrough, formed as a bundle of optical fibers, which is associated with a lighting lens system provided at the distal end of the flexible scope.

On the other hand, the video-signal processing unit includes a white-light source, such as a halogen lamp, a xenon lamp or the like. When the flexible scope is connected to the video-signal processing unit, the proximal end of the optical light guide is optically connected to the light source. Thus, an object to be photographed is illuminated by light radiating from the distal end of the optical light guide, and is focused as an optical image on a light-receiving surface of the CCD image sensor by the objective lens system.

The focused optical image is converted into a frame of analog image-pixel signals by the CCD image sensor. Then, the frame of analog image-pixel signals is read from the CCD image sensor by a CCD driver circuit provided in the flexible scope, and is fed to the video-signal processing unit, in which the image-pixel signals are suitably processed, thereby producing a video signal including image-pixel signals and various synchronizing signals. Then, the video signal is fed from the video-signal processing unit to a TV monitor to reproduce the photographed object on the monitor in accordance with the video signal.

The connection between the flexible scope and the video-signal processing unit is performed by the connection system including a connector, which comprises a set of connector halves. One of the connector halves is provided at the proximal end of the flexible scope, and the other connector half is provided in a housing wall of the video-signal processing unit. The connector half of the flexible scope has a plurality of contact pins which are electrically connected to various electric lines, such as an electric power line, a ground line, control-signal lines, image-signal lines and so on, extending to the CCD driver circuit and the image sensor, and the connector half of the video-signal processing unit also has a plurality of sheath-like contacts which are electrically connected to various electric lines, such as an electric power line, a ground line, control-signal lines, image-signal lines and so on, extending to a control circuit board of the video-signal processing unit. Namely, the CCD image sensor and the CCD driver circuit are electrically connected to the control circuit board of the video-signal processing unit via the connection between the connector halves.

In the conventional connection system, a user is obligated to turn OFF a power ON/OFF switch of the video-signal precessing unit when connecting the connector halves to each other, because undesirable and imprudent electric currents are produced between the power lines and the signal lines when a connection is established between the ground lines late after an establishment of a connection between the power lines and an establishment of connections between the signal lines. Nevertheless, the connection of the connector halves may be frequently carried out by the user while the power ON/OFF switch is turned ON.

Also, in the conventional connection system, when a contact pin and a sheath-like contact, exhibiting differing electrostatic potentials, are connected to each other, the electrostatic potential difference therebetween produces an electric current. Thus, conventionally, a by-pass diode is provided in each of the signal lines as a static-electricity-protector, to thereby eliminate a produced electric current from a signal line concerned via the by-pass diode. However, the by-pass diode is relatively costly as an electronic element, and thus the conventional connection system is expensive.

SUMMARY OF THE INVENTION

Therefore, an object of the present invention is to provide a connection system for establishing a connection between a flexible scope and a video-signal processing unit, wherein the establishment of the connection between the flexible scope and the video-signal processing unit can be properly performed under the condition in which an power ON/OFF switch of the video-processing unit is turned ON.

Another object of the present invention is to provide a connection system as mentioned above, which is arranged such that a low-cost static-electricity-protector can be provided in each of signal lines of the connection system.

In accordance with an aspect of the present invention, there is provided a connection system for establishing a detachable connection between a scope and a video-signal processing unit which form an electronic endoscope. The scope has a solid-state image sensor to produce image-pixel signals, and the video-signal processing unit has a processor for processing the image-pixel signals to produce a video signal. The scope includes a first power line, a first group of signal lines and a first ground line which are utilized to feed the image-pixel signals to the video-signal processing unit, and the video-signal processing unit includes a second power line, a second group of signal lines and a second ground line which are utilized to receive the image-pixel signals from the scope. The connection system comprises a connector that includes a first connector half provided on the scope, and a second connector half provided on the video-signal processing unit. The first power line, first group of signal lines and first ground line are connected to the second power line, second group of signal lines and second ground line, respectively, by establishing a connection between the first and second connector halves. The connection system also comprises a power switch element provided in one of the first and second power lines, and a power controller that changes an OFF-state of the power switch element to an ON-state after the respective connections are completely established between the first power line, first group of signal lines and first ground line and the second power line, second group of signal lines and second ground line.

Preferably, the power controller comprises a first power control line included in the scope, and a second power control line included in the video-signal processing unit. In this case, a connection between the first and second power control lines is established after the respective connections are completely established between the first power line, first group of signal lines and first ground line and the second power line, second group of signal lines and second ground line, and the change of the OFF-state of the power switch element to the ON-state is performed by the power controller when the connection is established between the first and second power control lines.

The power switch element may comprise a transistor which is arranged so as to be turned ON by the establishment of the connection between the first and second power control lines.

When the power switch element is provided in the second power line, the connection system may further comprise a switch circuit that controls an output of the video signal from the video-signal processing unit. In this case, an OFF-state of the switch circuit is changed to an ON-state when the change of the OFF-state of the power switch element to the ON-state is performed by the power controller, whereby the output of the video signal from the video-signal processing unit is enabled.

Furthermore, the connection system may comprise a monitor that reproduces an image on the basis of the output of the video signal from the video-signal processing unit, and a character-display-controller that displays a message on the monitor announcing the establishment of the complete connections between the first power line, first group of signal lines and first ground line and the second power line, second group of signal lines and second ground line when the change of the OFF-state of the power switch element to the ON-state is performed by the power controller.

Also, the connection system may further comprise an indicator that indicates the establishment of the complete connections between the first power line, first group of signal lines and first ground line and the second power line, second group of signal lines and second ground line when the change of the OFF-state of the power switch element to the ON-state is performed by the power controller. Preferably, the indicator comprises a light-emitting diode which is arranged so as to be lit when the change of the OFF-state of the power switch element to the ON-state is performed by the power controller.

Preferably, a transistor is provided in each of the signal lines included in the second group, and the transistor usually is in an ON-state such that the corresponding signal line is grounded, whereby the transistor serves as a static-electricity-protector for the corresponding signal. The ON-state of the transistor is changed to an OFF-state when the change of the OFF-state of the power switch element to the ON-state is performed by the power controller. In this case, a by-pass diode, which serves as a static-electricity-protector, may be provided in the second power control line.

In accordance with another aspect of the present invention, there is provided a connector which comprises a first connector half having a plurality of male contacts, and a second connector half having a plurality of female contacts. The respective male contacts are electrically connected to the female contacts when establishing a connection between the first and second connector halves, and one of the male contacts and a corresponding one of the female contacts are arranged so as to be electrically contacted to each other late after the respective connections are completely established between the remaining male contacts and the remaining female contacts.

Each of the male contacts may be formed as a contact pin, and each of the female contacts may be formed as a sheath-like contact. Also, the aforementioned one of the male contacts may be formed as a shorter pin than the remaining contact pins, and the aforementioned corresponding one of the female contacts is formed as a shorter sheath-like contact than the remaining sheath-like contacts.

BRIEF DESCRIPTION OF THE DRAWINGS

These objects and other objects of the present invention will be better understood from the following description, with reference to the accompanying drawings in which.

DESCRIPTION OF THE PREFERRED EMBODIMENT

Figure 1:
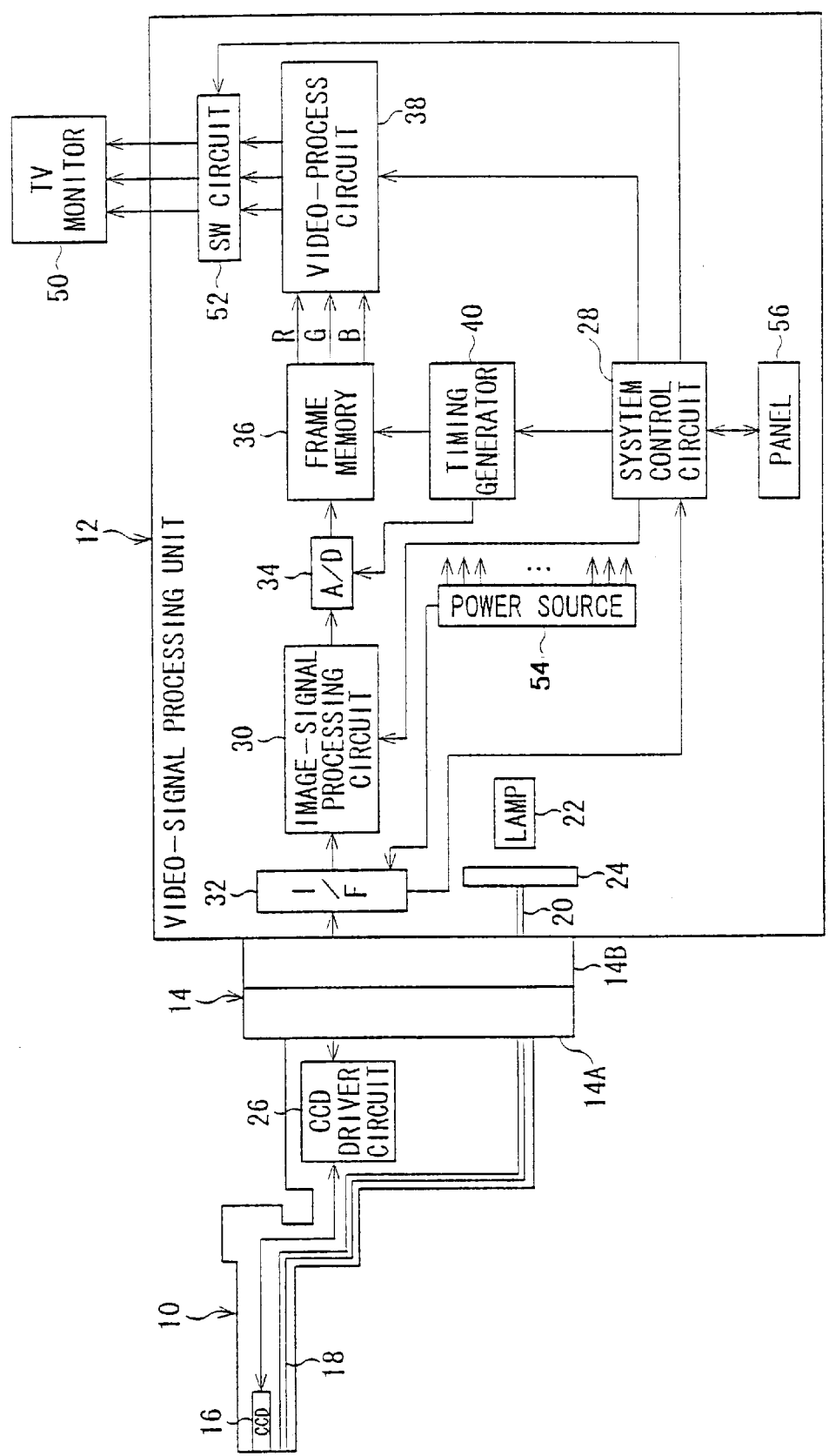
FIG. 1 is a schematic block diagram of an electronic endoscope in which a connection system, according to the present invention, for establishing a connection between the flexible scope and the video-signal processing unit is incorporated.

With reference to FIG. 1, an electronic endoscope, in which a connection system according to the present invention is embodied, is shown as a block diagram. In this electronic endoscope, a flexible conduit or scope 10 is detachably and manually connected to a video-signal processing unit 12 through the intermediary of a connector 14, symbolically and conceptually shown in FIG. 1, which forms a part of the connection system according to the present invention, and which comprises a set of connector halves 14A and 14B securely supported by the flexible scope 10 and the video-signal processing unit 12, respectively.

The flexible scope 10 includes an objective lens system (not shown) provided at the distal end thereof, and a solid-state image sensor 16, such as a CCD (charge-coupled-device) image sensor, associated therewith. An optical object to be photographed is focused, as an optical image, on a light-receiving surface of the CCD image sensor 16 by the objective lens system.

The flexible scope 10 also includes a flexible optical light guide 18 extended therethrough and formed as a bundle of optical fibers. The optical light guide 18 terminates at a light-radiating end face at the distal end of the flexible scope 10, and is associated with a lighting lens system (not shown) provided thereat. The proximal end of the flexible optical light guide 18 is securely and optically connected to one end of an optical light guide rod 20, which is supported by the connector half 14A of the connector 14 so as to protrude therefrom in a cantilever manner.

When the flexible scope 10 is connected to the video-signal processing unit 12 through the connector 14, the optical light guide rod 20 passes through the other connector half 14B of the connector 14, and then penetrates into the video-signal processing unit 12 such that a free end of the optical light guide rod 20 is optically connected to a white light source 22, such as a xenon lamp, a halogen lamp, or the like, provided in the video-signal processing unit 12. The light, emitted from the white-light source or lamp 22, is directed to the free end of the optical light guide rod 20, and then radiates as an illuminating-light from the distal end of the optical light guide 18. Thus, an object to be photographed by the CCD image sensor 16 is illuminated by light rays emitted from the distal end of the optical light guide 18 of the flexible conduit 10.

For reproduction of a photographed image as a color image, an RGB field sequential-type color imaging system is incorporated in the electronic endoscope. Thus, a rotary RGB color filter disk 24 is interposed between the free end of the optical light guide rod 20 and the white-light lamp 22. The rotary RGB color filter disk 24 is rotated at a predetermined rotational frequency in accordance with a chosen image-reproduction method, such as the NTSC system, the PAL system or the like, whereby an optical object to be photographed is sequentially illuminated by red light, green light and blue light. Namely, a red optical image, a green optical image and a blue optical image are sequentially and cyclically focused on the light-receiving surface of the CCD image sensor 16.

Note, in the NTSC system, the rotational frequency of the color filter disk 24 is 30 Hz, and, in the PAL system, the rotational frequency of the color filter disk 24 is 25 Hz.

Each of the red, green and blue optical images is sequentially converted into a frame of monochromatic (red, green, blue) analog image-pixel signals by the CCD image sensor 16, and the monochromatic analog image-pixel signals are successively read from the CCD image sensor 16. The reading of the monochromatic analog image-pixel signals from the CCD image sensor 16 is performed in accordance with a series of clock pulses, having a given frequency, output from a CCD driver circuit 26 provided in the flexible scope 10.

As shown in FIG. 1, the video-signal processing unit 12 is provided with a system control circuit 28, which may be constituted as a microcomputer, used to control the electronic endoscope as a whole, comprising, for example, a central processing unit (CPU), a read-only memory (ROM) for storing programs and constants, a random-access memory (RAM) for storing temporary data, and an input/output interface circuit (I/O).

The video-signal processing unit 12 is provided with an image-signal processing circuit 30, which is connected to the CCD driver circuit 26 through the intermediary of an interface circuit (I/F) 32 when the flexible scope 10 is connected to the video-signal processing unit 12 through the connecter 14. Note, the interface circuit 32 forms a part of the connection system according to the present invention, as discussed in detail hereinafter.

The monochromatic (red, green and blue) analog image-pixel signals, read from the CCD image sensor 14 by the CCD driver circuit 26, are fed to the image-signal processing circuit 30 through the interface circuit 32. In the image-signal processing circuit 30, the monochromatic image-pixel signals are subjected to various image-processings, such as a white-balance correction processing, a gamma-correction processing, a profile-enhancing processing and so on. Note, the reading of the monochromatic image-pixel signals from the CCD image sensor 16 by the CCD driver circuit 26 and the processing of the monochromatic image-pixel signals in the image-signal processing circuit 30 are performed under control of the system control circuit 28.

The monochromatic analog image-pixel signals, suitably processed in the image-signal processing circuit 30, are fed to an analog-to-digital (A/D) converter 34, and are converted by the A/D converter 34 into monochromatic digital image-pixel signals which are temporarily stored in a frame memory 36. In the frame memory 36, three frame memory sections are defined for the storage of red digital image-pixel signals, green digital image-pixel signals and blue digital image-pixel signals, respectively. In short, the monochromatic digital image-pixel signals are stored in a corresponding frame memory section defined in the frame memory 36.

Then, the respective red, green and blue digital image-pixel signals are simultaneously read from the three frame memory sections of the frame memory 36, and are output to a video-process circuit 38, as a red digital video signal R, a green digital video signal G and a blue digital video signal B, respectively. Namely, each of the red, green and blue digital video signals R, G and B is produced by suitably adding various synchronizing signals, such as horizontal synchronizing signals, vertical synchronizing signals and so on, to the monochromatic (red, green, blue) digital image-pixel signals read from the frame memory 36.

As shown in FIG. 1, the video-signal processing unit 12 is provided with a timing generator 40 which is operated under control of the system control circuit 28, whereby various types of clock pulses are produced by and output from the timing generator 40. For example, a series of sampling-clock-pulses is output from the timing generator 40 to the A/D converter 34, in which the conversion of the analog image-pixel signals into the digital image-pixel signals is carried out in accordance with the series of sampling-clock-pulses. Also, both a series of writing-clock-pulses and a series of reading-clock-pulses are output from the timing generator 40 to the frame memory 36, whereby the writing of the digital image-pixel signals in the frame memory 36 and the reading of the digital image-pixel signals from the memory 36 are carried out in accordance with the series of writing-clock-pulses and the series of reading-clock-pulses, respectively.

Figure 2:
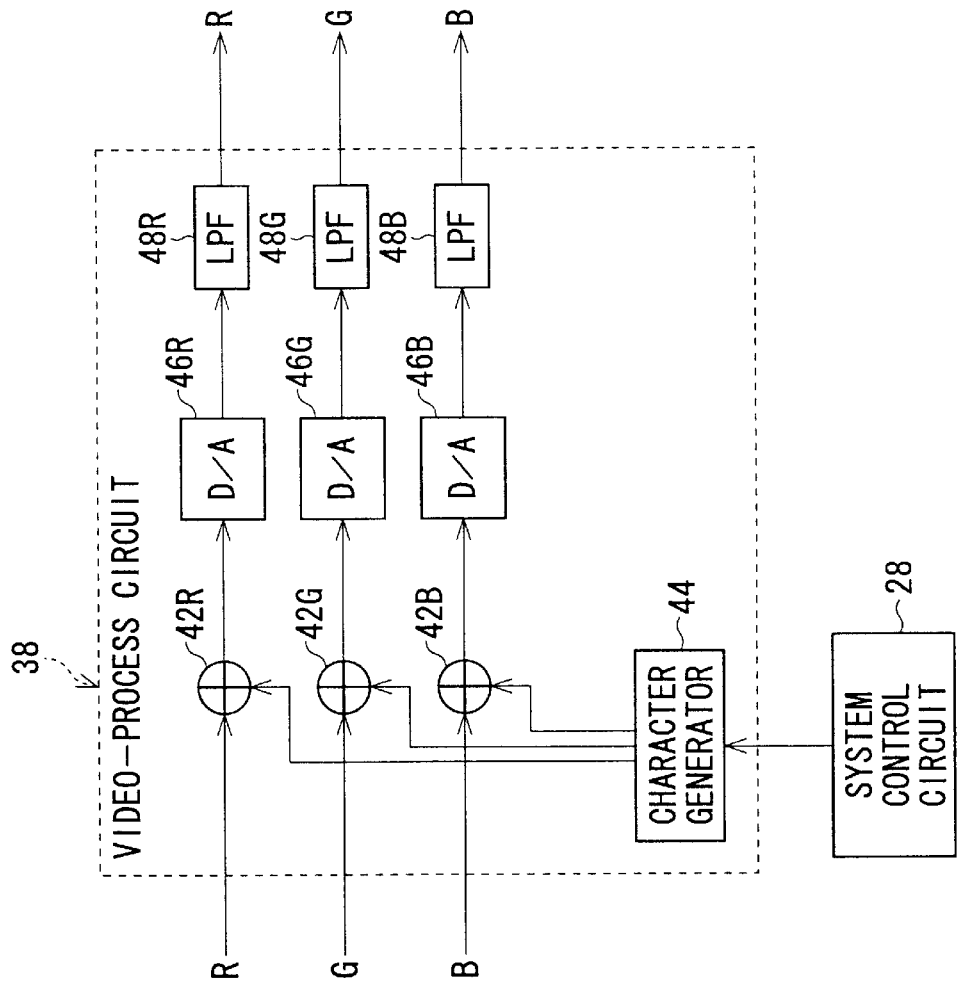
FIG. 2 is a schematic block diagram of a video-process circuit provided in the video-signal processing unit.

As shown in FIG. 2, the video-process circuit 38 is provided with three digital adders 42R, 42G and 42B, which are connected to the frame memory 36 to receive the red digital video signal R, the green digital video signal G and the blue digital video signals B therefrom, respectively, and which are connected to a digital character generator 44 to receive red digital character pattern signals, green digital character pattern signals and blue digital character pattern signals therefrom, when these digital character pattern signals are generated by the digital character generator 44. As is well known, the digital character generator 44 includes a memory, called "a video RAM (not shown)", and is operated under control of the system control circuit 28. When character code data is written in the video RAM, red, green and blue digital character pattern signals are generated on the basis of the character code data written in the video RAM. In short, the red, green and blue character pattern signals are added to the red, green and blue digital video signals (R, G and B) by the digital adders 42R, 42G and 42B, respectively, when necessary.

The video-process circuit 38 is further provided with digital-to-analog (D/A) converters 46R, 46G and 46B which are connected to the adders 42R, 42G and 42B, respectively, and low pass filters (LPF) 48R, 48G and 48B which are connected to the converters 46R, 46G and 46B, respectively. Consequently, the respective red, green and blue digital video signals R, G and B, output from the digital adders 42R, 42G and 42B, are converted into red, green and blue analog video signals by the D/A converters 46R, 46G and 46B, and the respective low pass filters 48R, 48G and 48B serve to eliminate high frequency signal components from the red, green and blue analog video signals R, G and B output from the D/A converters 46R, 46G and 46B.

As shown in FIG. 1, the video-process circuit 38 is connected to a TV monitor 50 through a switch circuit 52 which is operated under control of the system control circuit 28. When the switch circuit 52 is turned ON by the system control circuit 28, the red, green and blue analog video signals R, G and B, output from the video process circuit 38, are fed to the monitor 50 to reproduce and display the photographed color image thereon. Of course, when the red, green and blue analog video signals R, G and B carry the character pattern signals, character information data based on the character pattern signals are displayed together with the reproduced color image on the monitor 50. On the other hand, when the switch circuit 52 is turned OFF by the system control circuit 28, the feeding of the red, green and blue analog video signals R, G and B from the video process circuit 38 to the monitor 50 is forcibly stopped.

The character information data to be displayed on the monitor is classified into two groups: one group of variable character information data, such as a patient's name, a date and time of examination, examination comments and so on; and the other group of fixed character information data concerning predetermined various messages, such as "CONNECTION OF SCOPE IS COMPLETED", which especially relates to the present invention. The variable character code data corresponding to the variable character information data are written in the video RAM of the character generator 44 through a keyboard (not shown) which is connected to the system control circuit 28, if necessary. On the other hand, the fixed character code data corresponding to the fixed character information data are previously stored in the ROM of the system control circuit 28. If necessary, the fixed character code data are read from the ROM of the system control circuit 28, and are then written in the video RAM of the character generator 44.

As shown in FIG. 1, the interface circuit 32, which forms a part of the connection system according to the present invention, is connected to the system control circuit 28, if necessary. Namely, in a first embodiment of the connector system according to the present invention, it is unnecessary to connect the interface circuit 32 to the system control circuit 28, but, in a second embodiment of the connector system according to the present invention, it is necessary to connect the system control circuit 28.

In the second embodiment in which the interface circuit 32 is connected to the system control circuit 28, the interface circuit 32 produces and outputs a connection-indication signal, indicating whether a proper connection has been established between the connector halves 14A and 14B, to the system control circuit 28. In particular, when no connection has been established between the connector halves 14A and 14B, the connection-indication signal is maintained at low level, and, when a proper connection has been established between the connector halves 14A and 14B, the connection-indication signal is changed from the low level to a high level.

Also, in the second embodiment, the switch circuit 52 cannot be turned ON until it is confirmed by the system control circuit 28 that the connection-indication signal has changed from the low level to the high level. Namely, the switch circuit 52 is turned OFF while no connection has been established between the connector halves 14A and 14B.

Furthermore, when it is confirmed by the system control circuit 28 that the connection-indication signal has changed from the low level to the high level, a fixed character code data, corresponding to the aforementioned message "CONNECTION OF SCOPE IS COMPLETED", is read from the ROM of the system control circuit 28, and is then written in the video-RAM of the digital character generator 44, whereby the message "CONNECTION OF SCOPE IS COMPLETED" is displayed on the monitor 50. Namely, the display of the message "CONNECTION OF SCOPE IS COMPLETED" on the monitor 50 cannot be carried out until a proper connection is established between the connector halves 14A and 14B.

Note, in the first embodiment, in which the interface circuit 32 is not connected to the system control circuit 28, thereby producing no connection-indication signal, the switch circuit 52 is omitted, and thus the video-process circuit 38 is directly connected to the TV monitor 50. Also, note, in the first embodiment in which the interface circuit 32 produces no connection-indication signal, it is unnecessary to display the message "CONNECTION OF SCOPE IS COMPLETED" on the monitor 50.

As shown in FIG. 1, the video-signal processing unit 12 is provided with an electric power source circuit 54, by which various elements of the video-signal processing unit 12 are electrically energized under control of the system control circuit 28. Also, the CCD image sensor 16 and the CCD driver circuit 26 are connected to the power source circuit 54 through the connector 14 and the interface circuit 32, whereby it is possible to electrically energize the CCD image sensor 16 and the CCD driver circuit 26. In other words, the electrical energization of the CCD image sensor 16 and CCD driver circuit 26 cannot be carried out until a proper connection is established between the connector halves 14A and 14B.

Note, in FIG. 1, reference 56 indicates a manipulation panel 56, in which various switches, such as a power ON/OFF switch for the video-signal processing unit 12, a lamp ON/OFF switch for the lamp 22 and so on, are provided.

Figure 3:
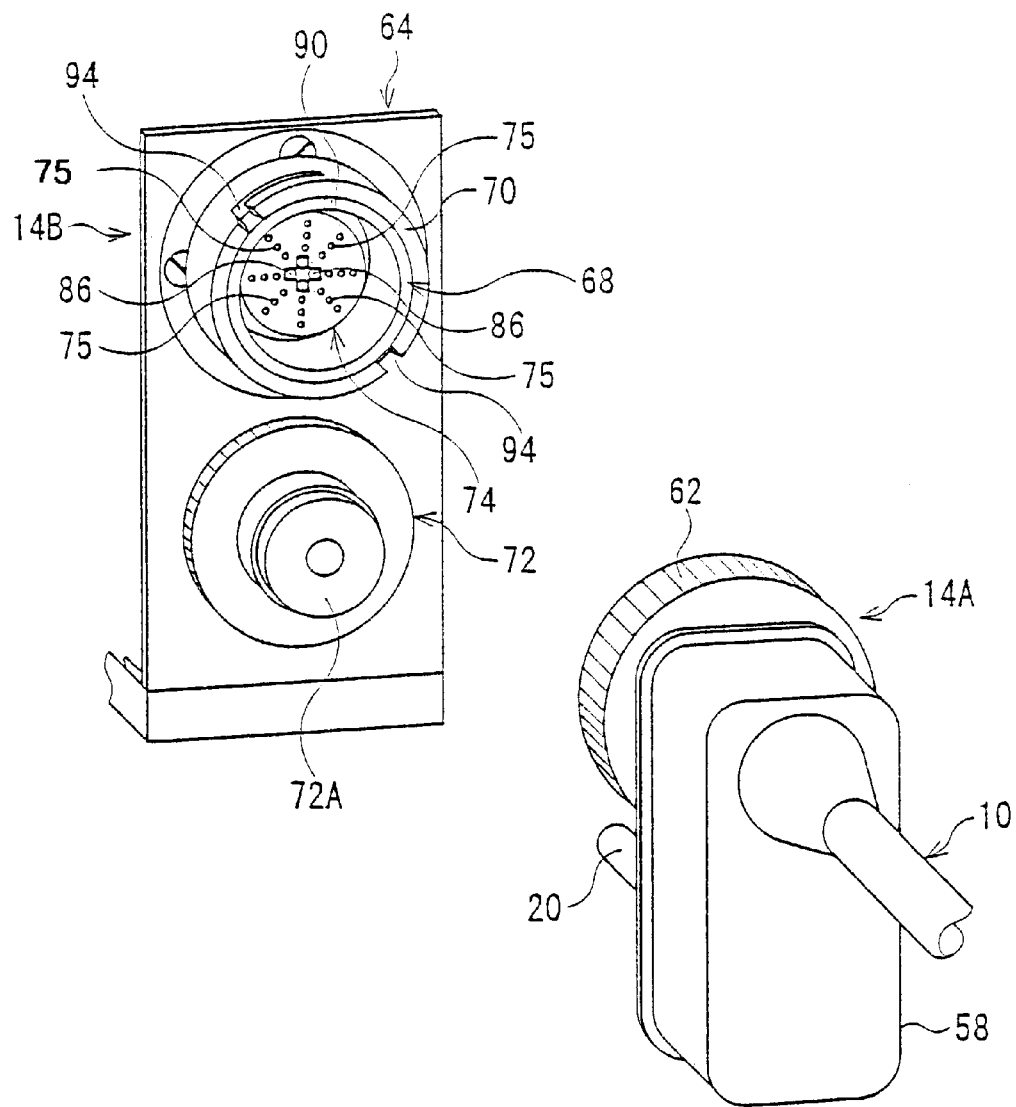
FIG. 3 is a perspective view of a connector comprising a set of connector halves which forms a part of the connection system according to the present invention.
Figure 4:
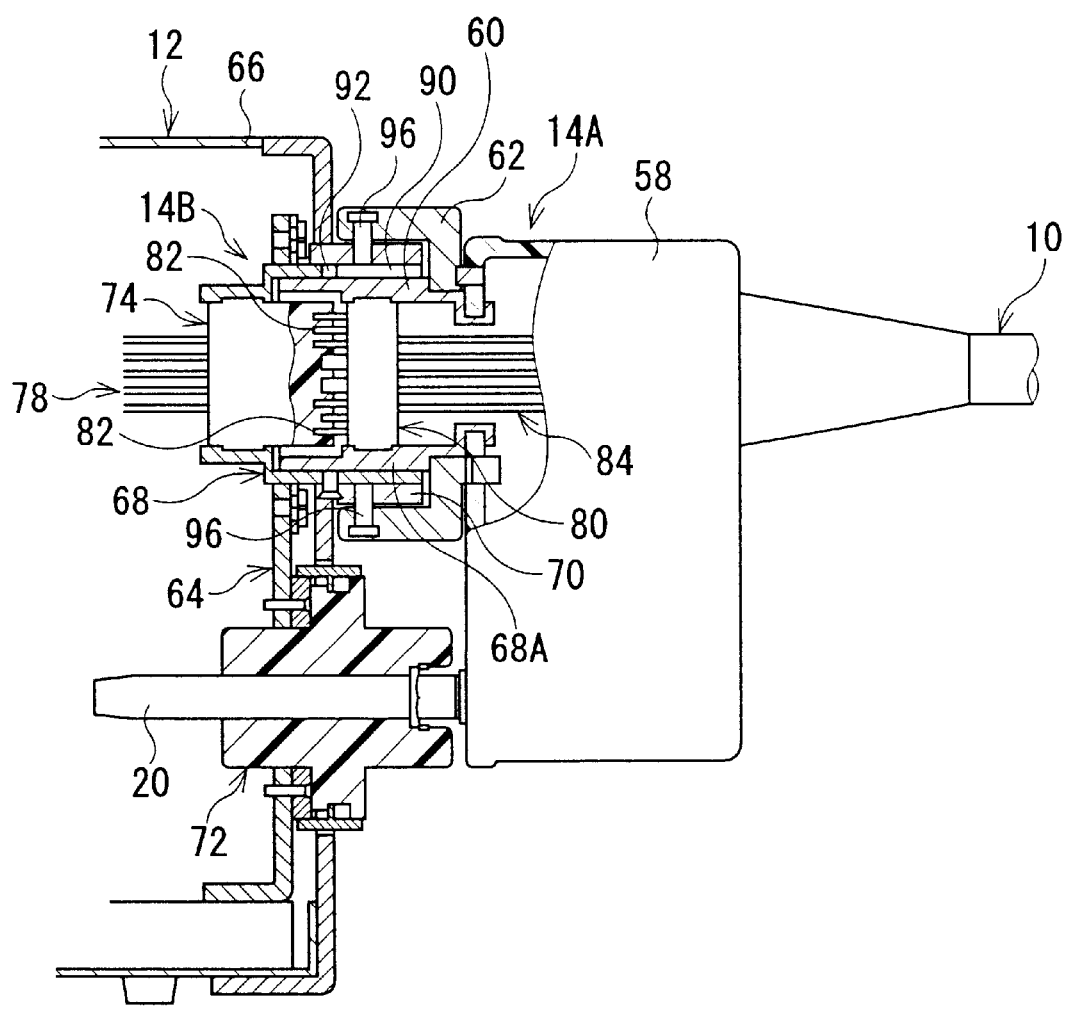
FIG. 4 is a partial cross-sectional side view showing the connector halves connected to each other.

With reference to FIGS. 3 and 4, the connector halves 14A and 14B of the connector 14 are illustrated. Note, in FIG. 3, the connector halves 14A and 14B are disconnected from each other, and, in FIG. 4, the connector halves 14A and 14B are connected to each other.

The connector half 14A comprises a box-like casing 58, which may be formed of a suitable synthetic resin material. The proximal end of the flexible scope 10, which is shaped as a frustum-conical end, is securely joined to a front side of the box-like casing 58, and the optical light guide rod 20 protrudes from a rear side of the box-like casing 58 in a cantilever manner. Also, the connector half 14A comprises a coupler ring member 60 securely supported by and protruding from a rear side of the box-like casing 58 (FIG. 4), and a manipulating ring member 62 rotatably mounted on the coupler ring member 60. Preferably, the ring members 60 and 62 are formed of a suitable metal material.

Of course, although not visible in FIGS. 3 and 4, the inner end of the optical light guide rod 20 is optically connected to the proximal end of the flexible optical light guide 18 extending through the flexible scope 10. Also, the CCD driver circuit 26 is housed as a printed circuit board in the box-like casing 58, and is electrically connected to the CCD image sensor 16 through various electric lines, such as an electric power line, a ground line, control-signal lines, image-signal lines and so on, extending through the flexible scope 10.

On the other hand, the connector half 14B comprises a rectangular plate member 64 securely attached to and supported by a housing 66 of the video-signal processing unit 12, which is partially shown in FIG. 4. The connector half 14B also comprises a sleeve member 68 which is securely fitted and fixed in a circular opening formed in the rectangular plate member 64. A wall of the housing 66 has a circular opening formed therein, and a forward portion 68A of the sleeve member 68 passes through the circular opening of the housing wall (66) so as to outwardly protrude therefrom. The forward or outward portion 68A of the sleeve member 68 has a cam ring member 70 securely mounted thereon, and is engaged with both the coupler ring member 60 and the manipulating ring member 62 in a manner stated in detail hereinafter. Note, the members 64, 68 and 70 may be formed of a suitable metal material.

The rectangular plate member 64 has another circular opening formed therein, which is located at a lower position than that of the aforementioned circular opening of the plate member 64 in which the sleeve member 68 is fitted. The connector half 14B comprises an adapter socket 72 for receiving the optical light guide rod 20, and the adapter socket 72 is securely fitted and fixed in the other circular opening of the rectangular plate 64. When the connector halves 14A and 14B are connected to each other, as shown in FIG. 4, the optical light guide rod 20 is inserted in the adapter socket 72, and is positioned such that a free end of the optical light guide rod 20 is optically connected to the lamp 22. Note, the adapter socket 72 is preferably formed of a suitable synthetic resin material.

As best shown in FIG. 4, the sleeve member 68 has a plug-like isolator element 74 securely fitted therein, and the isolator element 74 may be formed of a suitable synthetic resin material. As best shown in FIG. 3, the isolator element 74 has a plurality of pin-socket holes 75 formed in an outer end face thereof, and these pin-socket holes 75 are radially arranged with respect to a central axis of the isolator element 74.

Figure 5:
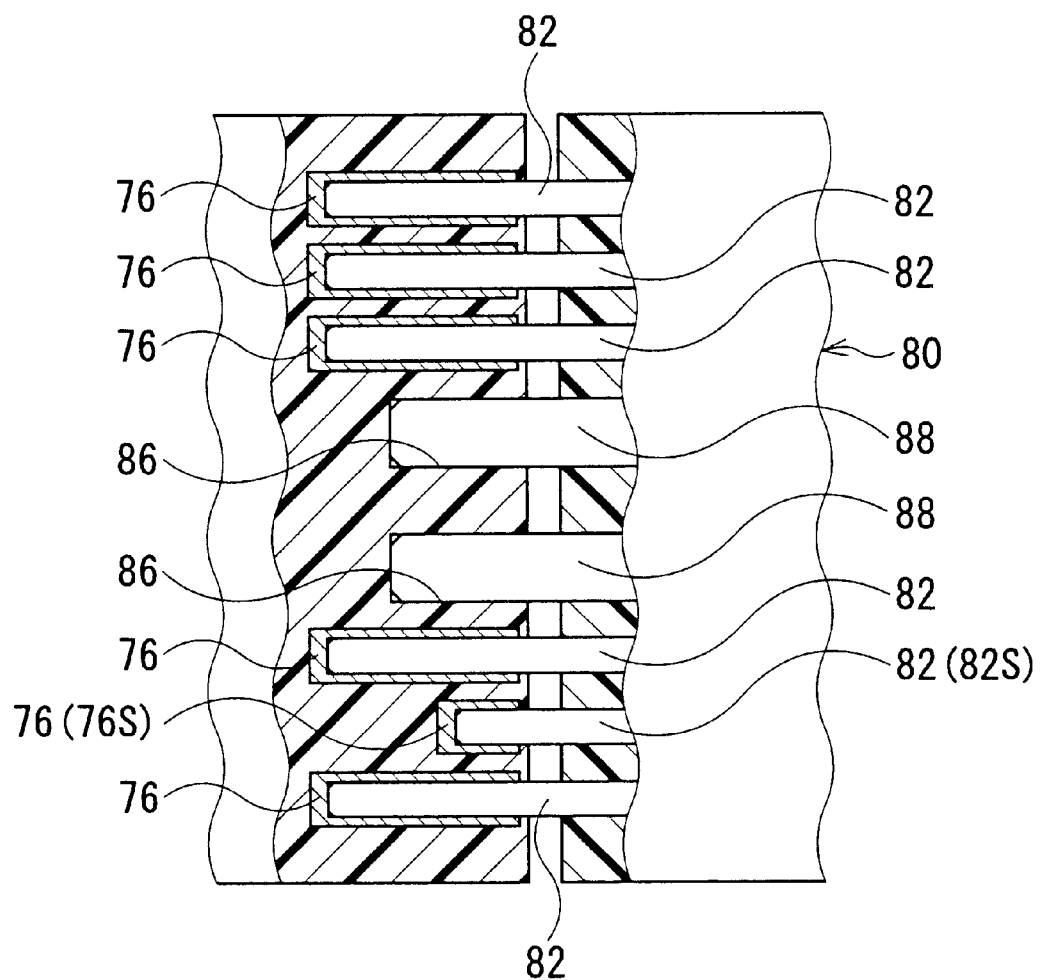
FIG. 5 is a partial cross-sectional side view of two isolator elements provided in the connector halves and having a plurality of connector pins and a plurality of sheath-like contacts, respectively, with the respective connector pins being completely inserted into the sheath-like contacts.

As shown in FIG. 5, a sheath-like contact 76 is securely inserted in each of the pin-socket holes 75, and is formed of a suitable electrically conductive material, such as copper, brass or the like. The respective sheath-like contacts 76 are electrically connected to electric lines, generally indicated by reference 78 in FIG. 4, embedded in the isolator element 74 and extended from an inner end face thereof. Of course, the electric lines 78 are electrically connected to a printed circuit board (not shown), on which various electronic elements, inclusive of the elements 28, 32, 30, 34, 36, and so on, are mounted.

Similarly, as shown in FIG. 4, the coupler ring member 60 of the connector half 14A has a plug-like isolator element 80 securely fitted therein, which may be formed of a suitable synthetic resin material. The isolator element 80 has a plurality of contact pins 82 embedded therein so as to protrude from an outer end face thereof, and the contact pins 82 are formed of a suitable electrically conductive material, such as copper, brass or the like. The contact pins 82 are radially arranged in the same manner as the pin-socket holes 75, such that the respective contact pins 82 can be aligned with the pin-socket holes 75. The respective contact pins 82 are electrically connected to electric lines, generally indicated by reference 84 in FIG. 4, embedded in the isolator element 80 and extended from an inner end face thereof. Of course, the electric lines 84 are electrically connected to the CCD driver circuit 26 housed in the box-like casing 58.

As is apparent from FIG. 3, a number of pin-socket holes 75 is twenty four, and the isolator element 80 has the same number of contact pins 82 as the pin-socket holes 75. Also, the isolator element 74 has four guide holes 86 formed in a central area of the outer end face thereof, and the isolator element 80 has four guide pins 88 extended from a central area of the outer end face thereof. The four guide holes 86 and the four guide pins 88 are arranged such that the respective guide holes 86 can be aligned with the guide pins 88.

With the aforementioned arrangement, when the connector halves 14A and 14B are connected to each other, the contact pins 82 and guide pins 88 of the connector half 14A can be inserted in the pin-socket holes 75 and guide holes 86 of the connector half 14B, as shown in FIG. 5, whereby it is possible to establish respective electrical connections between the contact pins 82 and the sheath-like contacts 76.

In order to ensure a manual proper connection between the connector halves 14A and 14B, the outward portion 68A of the sleeve member 68 is formed with a positioning slot 90 extending in parallel with a central axis thereof, as shown in FIGS. 3 and 4, and the coupler ring member 60 is formed with a positioning projection 92 radially and outwardly protruding therefrom (FIG. 4). The positioning projection 92 is configured so as to be slidably fit into the positioning slot 90, and thus the coupler ring member 60 can be inserted into the sleeve member 68 only when the connector half 14A is oriented with respect to the connector half 14B such that the positioning projection 92 is aligned with the positioning slot 90. Also, only when the alignment is established between the positioning projection 92 and the positioning slot 90, can the contact pins 82 and guide pins 88 be in alignment with the pin-socket holes 75 and guide holes 86, respectively. Namely, when the positioning projection 92 is received in the positioning slot 90, the alignment between the contact pins 82 and guide pins 88 and the pin-socket holes 75 and guide holes 86 is ensured.

Figure 6:
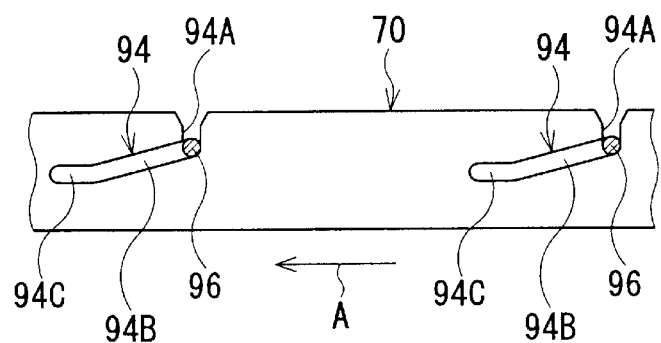
FIG. 6 is a partial development view of a cam ring member of the connector.

Furthermore, as shown in FIG. 3, the cam ring member 70 is formed with a pair of diametrically-opposed cam grooves 94, and the rotatable manipulating ring member 62 is provided with a pair of diametrically-opposed cam pins 96 radially and inwardly protruding therefrom (FIG. 4). Of course, each of the cam pins 96 is configured so as to be slidably fit into one of the cam grooves 94. As best shown in FIG. 6, each of the cam grooves 94 includes an entrance section 94A, a slant section 94B which extends from the entrance section 94 in a direction indicated by an arrow A, and an end section 94c at which the slant section 94B terminates.

With the aforementioned arrangement, it is possible to easily and manually establish a connection between the connector halves 14A and 14B. In particular, firstly, the coupler ring member 60 is inserted into the sleeve member 68 in the aforementioned manner, with the positioning projection 92 being received in the positioning slot 90. Secondly, the rotatable manipulating ring member 62 is manually oriented such that the cam pins 96 are received in the entrance sections 94A, and is then rotated in the direction indicated by the arrow A, so that the coupler ring member 60 is thrust toward the outer end face of the isolator element 74. Thus, as shown in FIG. 7, it is possible to ensure the insertion of the contact pins 82 and guide pins 88 into the pin-socket holes 75 and guide holes 86, respectively, because the alignment between the contact pins 82 and guide pins 88 and the pin-socket holes 75 and guide holes 86 is ensured due to the positioning projection 92 being received in the positioning slot 90.

Figure 7:
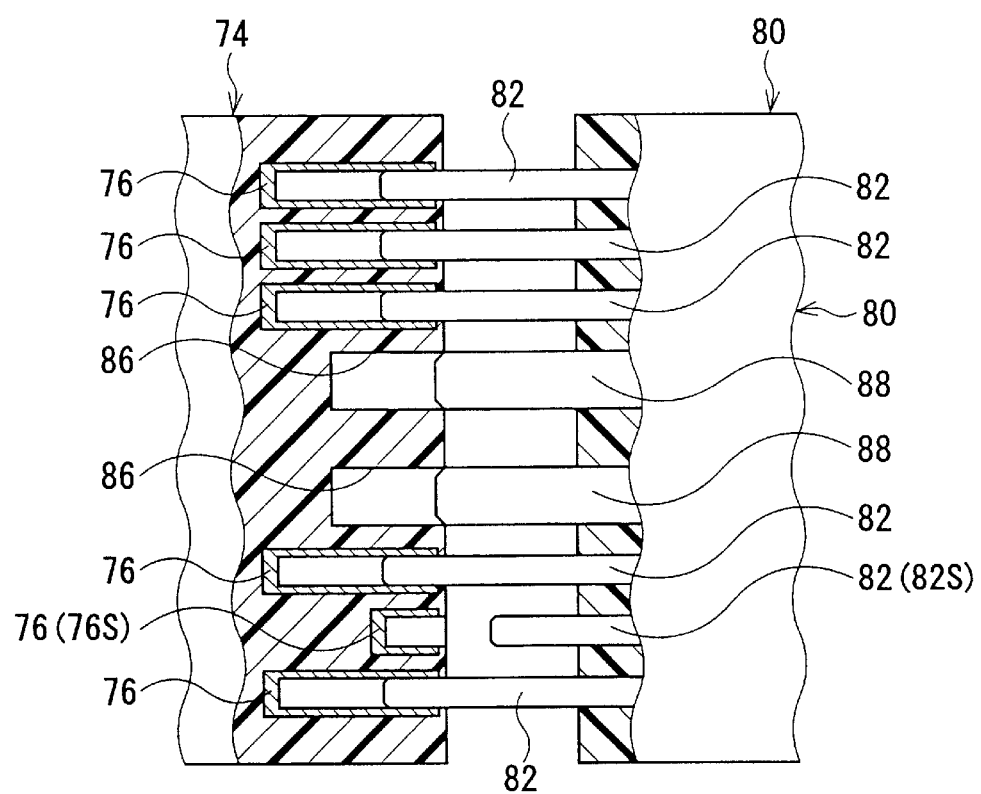
FIG. 7 is a partial cross-sectional side view, similar to FIG. 5, with the respective connector pins being partially inserted into the sheath-like contacts.

As best shown in FIGS. 5 and 7, only one of the contact pins 82, indicated by bracketed sub-reference 82S, is shorter than the remaining contact pins 82, and a corresponding pin-socket hole, in which the short contact pin 82S is inserted, is shallower than the remaining pin-socket holes 75. Note, in FIG. 5, a sheath-like contact 76, fitted in the shallower pin-socket hole concerned, is indicated by bracketed sub-reference 76S. Thus, as shown in FIG. 7, an electrical connection is always established late between the short sheath-like contact 76S and the short contact pin 82S. Namely, the establishment of the electrical connection between the short sheath-like contact 76S and the short contact pin 82S does not occur until electrical connections are established between the remaining sheath-like contacts 76 and the remaining contact pins 82. For the present invention, this feature is very significant for the reasons discussed hereinafter.

Figure 8:
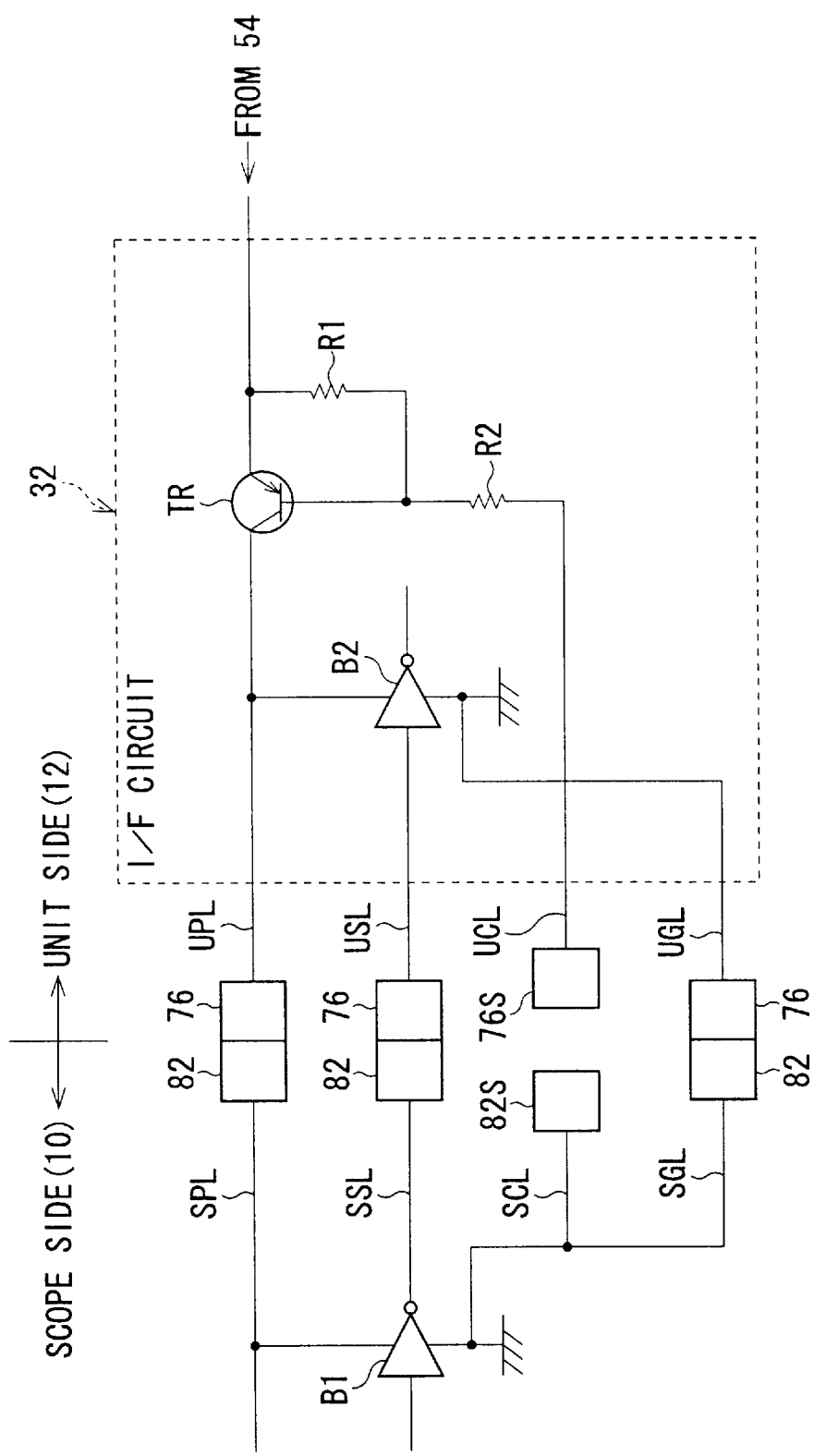
FIG. 8 is a wiring diagram of a first embodiment of the connector system according to the present invention, in which a short contact pin and a short sheath-like contact are not connected.
Figure 9:
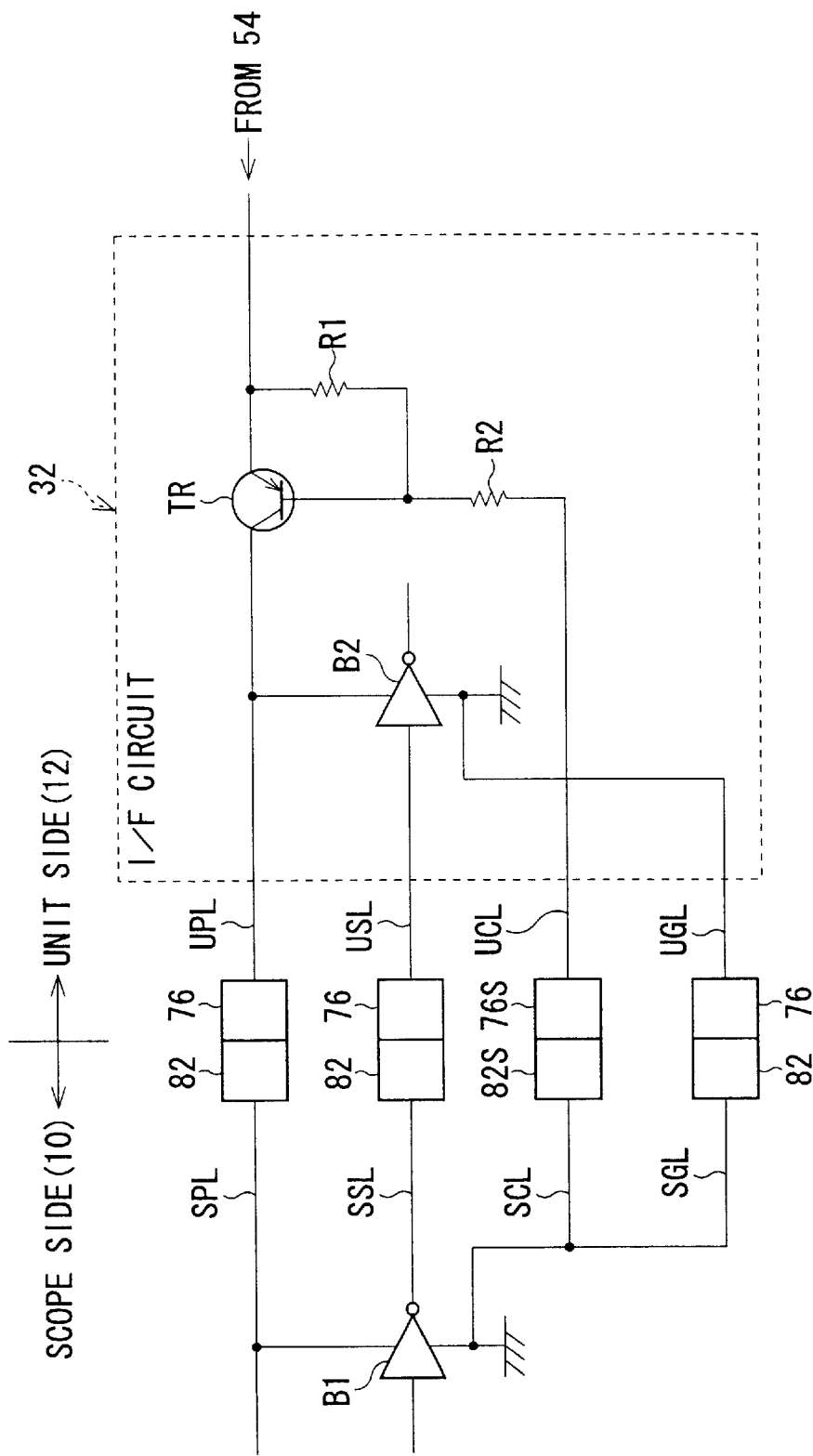
FIG. 9 is a wiring diagram, similar to FIG. 8, in which a short contact pin and a short sheath-like contact are connected.

With reference to FIGS. 8 and 9, the first embodiment of the connection system according to the present invention is shown as a wiring diagram, and the interface circuit 32, forming a part of the connection system, is arranged as shown in these drawings. As mentioned previously, in the first embodiment, the interface circuit 32 is not connected to the system control circuit 28, and the switch circuit 52 is omitted.

In the connector half 14A of scope side (10), the electric lines 84, extending between the CCD driver circuit 26 and the contact pins 82 of the connector half 14A, comprises a power line, various signal lines including control-signal lines and image-pixel signal lines, a power control line, and a ground line. In FIGS. 8 and 9, the power line is indicated by reference SPL; a representative of the various signal lines is indicated by reference SSL; the power control line is indicated by reference SCL; and the ground line is indicated by reference SGL. Note, the short connector pin 82S is designated as the power control line SCL.

Similarly, in the connector half 14B or unit side (12), the electric lines 78, extending between the interface circuit 32 and the sheath-like contacts 76 of the connector half 14B, comprises a power line, various signal lines including control-signal lines and image-pixel signal lines, a power control line, and a ground line. In FIGS. 8 and 9, the power line is indicated by reference UPL; a representative of the various signal lines is indicated by reference USL; the power control line is indicated by reference UCL; and the ground line is indicated by reference UGL. Note, the short sheath-like contact 76S is designated as the power control line UCL.

In the scope side (10), the power line SPL is connected to a corresponding contact pin 82 at one end thereof, and is connected to the CCD driver circuit 26 at the other end thereof, with the power line SPL being further extended to the CCD image sensor 16. On the other hand, in the unit side (12), the power line UPL is connected to a corresponding sheath-like contact 76 at one end thereof, and is connected to the power source circuit 54 at the other end thereof. As shown in FIGS. 8 and 9, a PNP-type transistor TR, which serves as a switch element, is provided in the power line UPL such that a collector of the transistor TR is connected to the sheath-like contact 76 concerned; an emitter of the transistor TR is connected to the power source circuit 54; and a base of the transistor TR is connected to the emitter thereof via a resistance R1.

In the scope side (10), the representative signal line SSL is connected to a corresponding contact pin 82 at one end thereof, and is connected to the CCD driver circuit 26 at the other end thereof, with the signal line SSL being further extended to the CCD image sensor 16, and having a buffer B1 provided therein. Of course, this is true for the remaining signal lines of the scope side (10). On the other hand, in the unit side (12), the representative signal line USL is connected to a corresponding sheath-like contact 76 at one end thereof, and is connected to the image-signal processing circuit 30 at the other end thereof, with the signal line SSL having a buffer B2 provided therein. Of course, this is true for the remaining signal lines of the unit side (12).

In the scope side (10), the power control line SCL is connected to the short contact pin 82S at one end thereof, and is grounded at the other end thereof. On the other hand, in the unit side (12), the power control line UCL is connected to the short sheath-like contact 76S at one end thereof, and is connected to the base of the transistor TR via a resistance R2 at the other end thereof.

In the scope side (10), the ground line SGL is connected to a corresponding contact pin 82 at one end thereof, and is grounded at the other end thereof. Note, the power line SPL is grounded via the buffer B1. Similarly, in the unit side (12), the ground line UGL is connected to a corresponding sheath-like contact 76 at one end thereof, and is grounded at the other end thereof. Note, the power line UPL is grounded via the buffer B2.

With the aforementioned arrangement of the connection system, under the condition in which the power ON/OFF switch of the video-signal precessing unit 12 is turned ON, electrical connections can be properly established between the contact pins 82 of the connector half 14A and the sheath-like contacts 76 of the connector half 14B without producing any undesirable and imprudent electric current in the signals lines (SSL and USL).

In particular, although the power ON/OFF switch of the video-signal processing unit 12 is turned ON, the sheath-like contact 76 per se of the power line UPL cannot be electrically powered because the transistor TR is at an OFF-state. Namely, when a power voltage is applied from the power source circuit 54 to the emitter of the transistor TR by turning the power ON/OFF switch ON, a given voltage is simultaneously applied to the base of the transistor TR in accordance with a resistance value of the resistance R1. Thus, since the transistor TR is at the OFF-state, the power voltage cannot be applied to the sheath-like contact 76 of the power line UPL.

When the connector halves 14A and 14B are connected to each other in the aforementioned manner, the contact pins 82 of the power line SPL, signal line SSL and ground line SGL are preliminarily connected to the sheath-like contacts 76 of the power line UPL, signal line USL and ground line UGL, prior to the establishment of the connection between the short contact pin 82S of the power control line SCL and the short sheath-like contact 76S of the power control line UCL. Accordingly, although the connection is established between the contact pin 82 of the power line SPL and the sheath-like contact 76 of the power line UPL, the power line SPL of the connector half 14A cannot be electrically powered until the short contact pin 82S of the power control line SCL is connected to the short sheath-like contact 76S of the power control line UCL, as shown in FIG. 8.

When the connection is established between the short contact pin 82S of the power control line SCL and the short sheath-like contact 76S of the power control line UCL, as shown in FIG. 9, the base of the transistor TR is grounded so that the given voltage applied thereto is decreased to a ground level. Thus, the OFF-state of the transistor TR is changed to an ON-state, whereby the power line SPL of the connector half 14A is electrically powered, thereby electrically energizing the CCD driver circuit 26 and the CCD image sensor 16, without producing any undesirable and imprudent electric current in the signals lines (SSL and USL), because the establishment of the connection between the ground lines SGL and UGL is completely ensured whenever the power lines SPL and UPL of the connector 14 are electrically powered.

Figure 10:
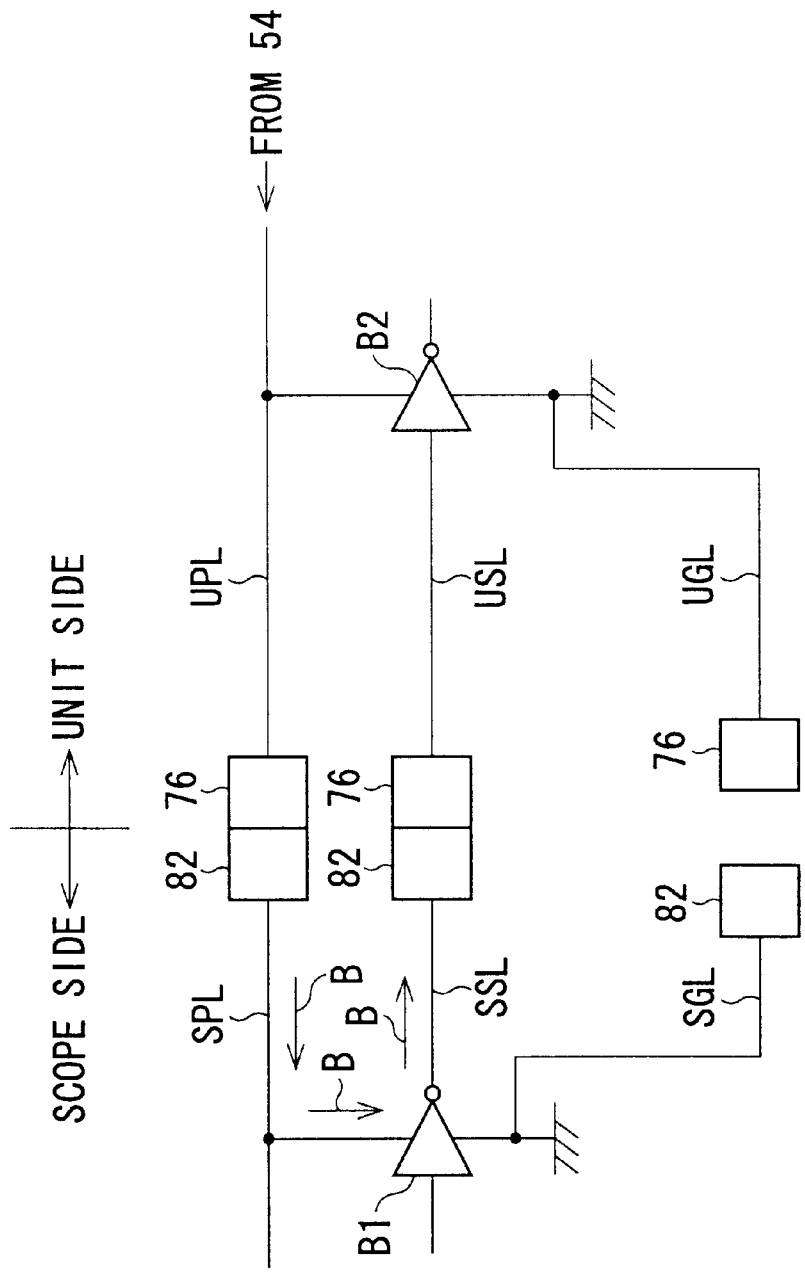
FIG. 10 is a wiring diagram of a conventional connector system incorporated in an electronic endoscope as shown in FIG. 1.

With reference to FIG. 10, a conventional arrangement of a connection system, incorporated in an electronic endoscope as shown in FIG. 1, is illustrated. Note, in FIG. 10, the features similar to those of FIGS. 8 and 9 are indicated by the same references, respectively.

In the conventional connection system, when connector halves (14A and 14B) are connected to each other, a case may frequently occur in which a contact pin 82 of a ground line SGL is connected to a sheath-like contact 76 of a ground line UGL late after establishment of connections between contact pins 82 of a power line SPL and a signal line SSL and sheath-like contacts 76 of a power line UPL and a signal line USL, as shown in FIG. 10. In this case, undesirable and imprudent electric currents are produced between the power lines SPL and UPL and the signal lines SSL and USL, as indicated by arrows B in FIG. 10. Consequently, the production of the undesirable and imprudent electric currents may result in malfunction of the electronic endoscope and in damage of electronic devices included in the electronic endoscope. Accordingly, in the conventional connection system, when the connector halves (14A and 14B) are connected to each other, a user is obligated to turn OFF a power ON/OFF switch of a video-signal precessing unit (12).

Figure 11:
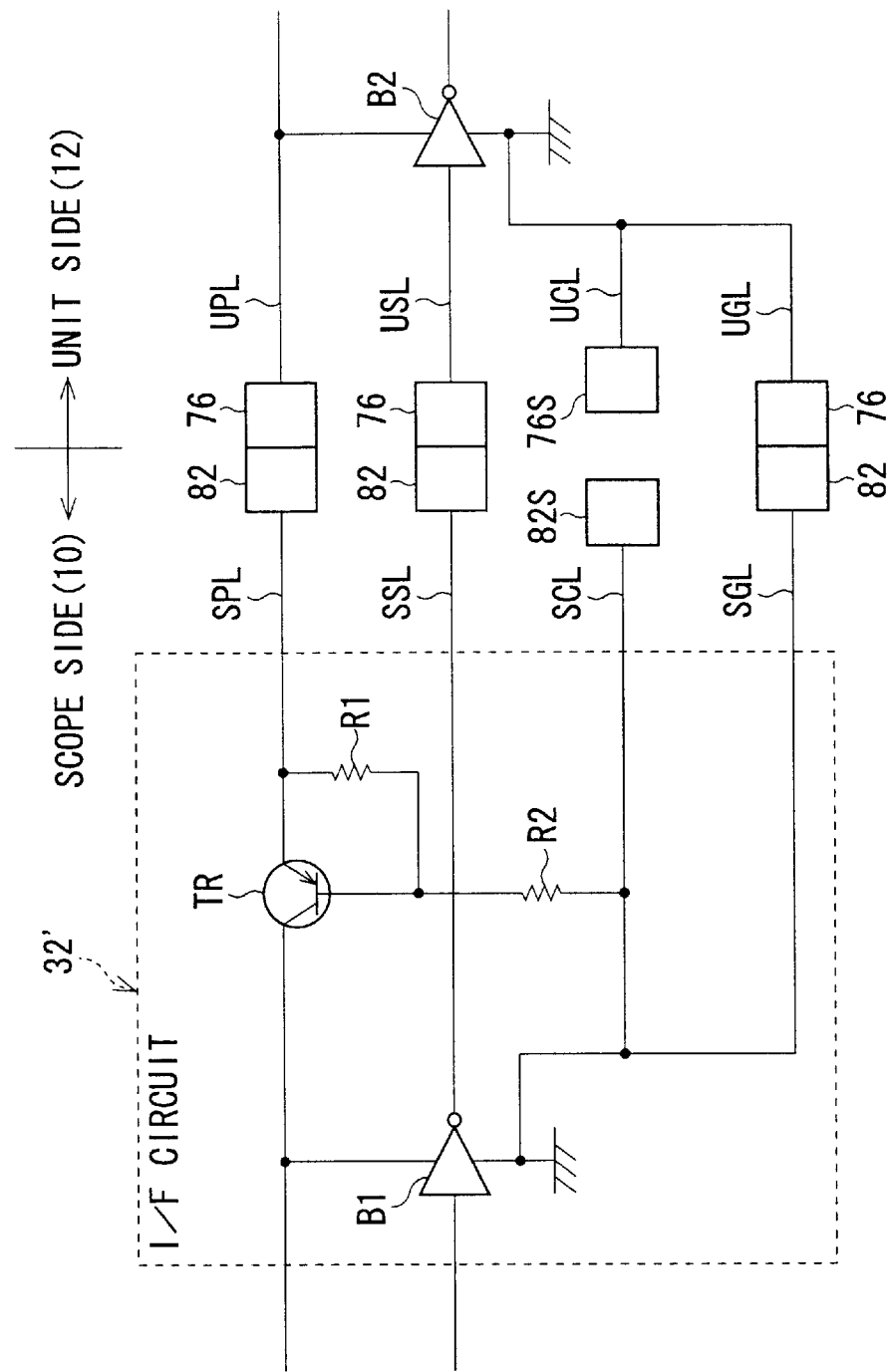
FIG. 11 is a wiring diagram of a modification of the first embodiment of the connector system according to the present invention.

FIG. 11 shows a modification of the first embodiment of the connection system according to the present invention. Note, in FIG. 11, the features similar to those of FIGS. 8 and 9 are indicated by the same references, respectively.

In the modified connection system, an interface circuit 32' is incorporated in the scope side (10), and is arranged in substantially same manner as the interface circuit 32 shown in FIGS. 8 and 9.

Similar to the first embodiment of the connection system, although the contact pin 82 of the power line SPL and the sheath-like contact 76 of the power line UPL are connected to each other, the transistor TR is maintained in an OFF-state until the short contact pin 82S and the short sheath-like contact 76S are connected to each other. Of course, when the connection is established between the short contact pin 82S and the short sheath-like contact 76S, the OFF-state of the transistor TR is changed to an ON-state, thereby electrically energizing the CCD driver circuit 26 and the CCD image sensor 16, without producing any undesirable and imprudent electric current in the signals lines (SSL and USL).

Figure 12:
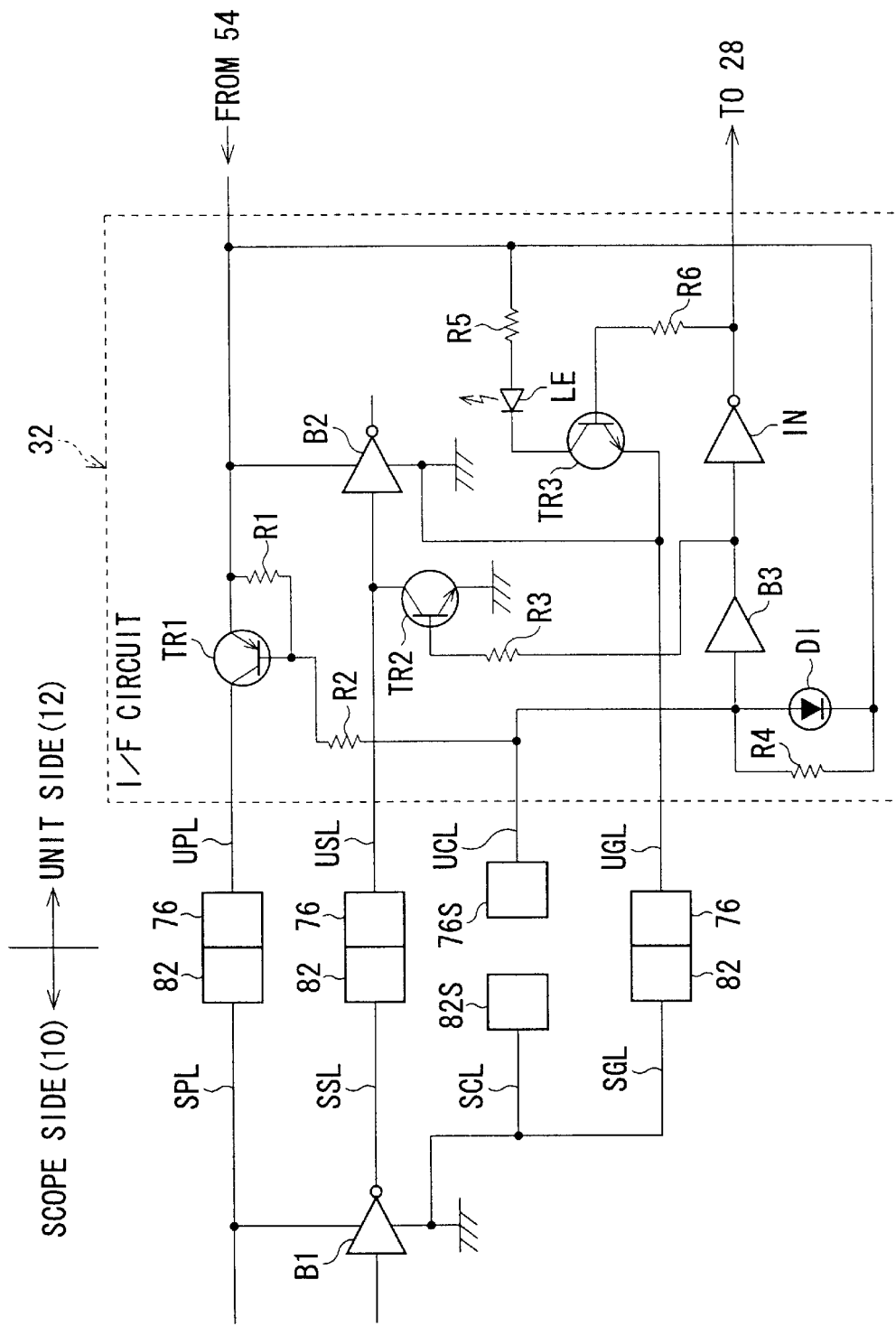
FIG. 12 is a wiring diagram of a second embodiment of the connector system according to the present invention, in which a short contact pin and a short sheath-like contact are not connected.
Figure 13:
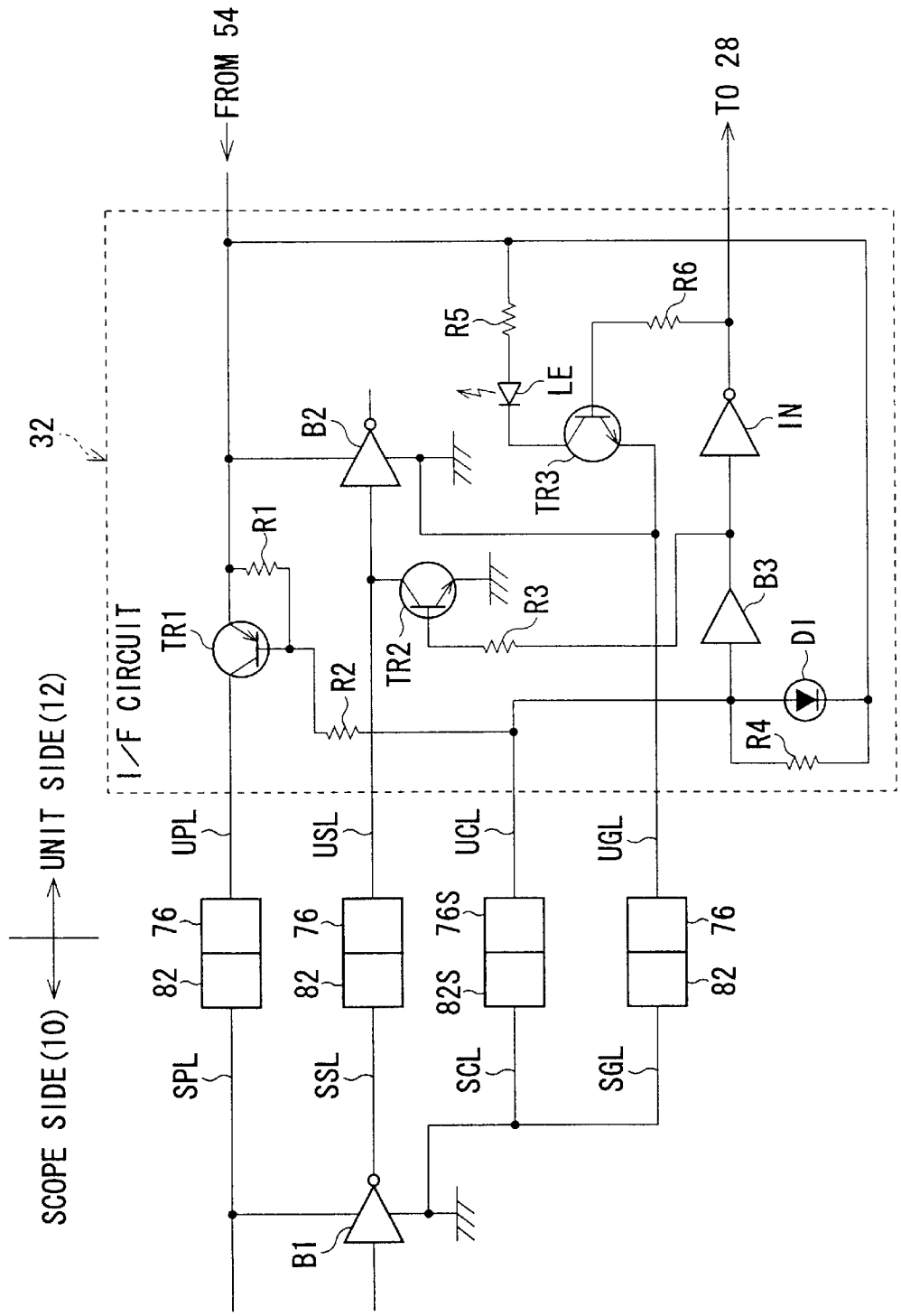
FIG. 13 is a wiring diagram, similar to FIG. 12, in which a short contact pin and a short sheath-like contact are connected.

With reference to FIGS. 12 and 13, the second embodiment of the connection system according to the present invention is shown as a wiring diagram, and the interface circuit 32, forming a part of the connection system, is arranged as shown in these drawings. As mentioned above, in the second embodiment, the interface circuit 32 is connected to the system control circuit 28, and the switch circuit 52 is interposed between the video-process circuit 38 and the TV monitor 50. Note, in FIGS. 12 13, the features similar to those of FIGS. 8 and 9 are indicated by the same references, respectively.

Similar to the first embodiment, a power line SPL is connected to a corresponding contact pin 82 at one end thereof, and is connected to the CCD driver circuit 26 at the other end thereof, with the power line SPL being further extended to the CCD image sensor 16. Also, a power line UPL is connected to a corresponding sheath-like contact 76 at one end thereof, and is connected to the power source circuit 54 at the other end thereof. As shown in FIGS. 12 and 13, a PNP-type transistor TR1, which serves as a switch element, is provided in the power line UPL such that a collector of the transistor TR1 is connected to the sheath-like contact 76 concerned; an emitter of the transistor TR1 is connected to the power source circuit 54; and a base of the transistor TR1 is connected to the emitter thereof via a resistance R1.

Similar to the first embodiment, a representative signal line SSL is connected to a corresponding contact pin 82 at one end thereof, and is connected to the CCD driver circuit 26 at the other end thereof, with the signal line SSL being further extended to the CCD image sensor 16, and having a buffer B1 provided therein. Of course, this is true for the remaining signal lines of the scope side (10). Also, a representative signal line USL is connected to a corresponding sheath-like contact 76 at one end thereof, and is connected to the image-signal processing circuit 30 at the other end thereof, with the signal line SSL having a buffer B2 provided therein. Of course, this is true for the remaining signal lines of the unit side (12).

Similar to the first embodiment, a power control line SCL is connected to the short contact pin 82S at one end thereof, and is grounded at the other end thereof. Also, a power control line UCL is connected to the short sheath-like contact 76S at one end thereof, and is connected to the base of the transistor TR1 via a resistance R2 at the other end thereof.

Similar to the first embodiment, a ground line SGL is connected to a corresponding contact pin 82 at one end thereof, and is grounded at the other end thereof. Note, the power line SPL is grounded via the buffer B1. Also, a ground line UGL is connected to a corresponding sheath-like contact 76 at one end thereof, and is grounded at the other end thereof. Note, the power line UPL is grounded via the buffer B2.

In short, the aforementioned arrangement of the second embodiment is substantially identical to that of the first embodiment. Accordingly, under the condition in which the power ON/OFF switch of the video-signal precessing unit 12 is turned ON, electrical connections can be properly established between the contact pins 82 of the connector half 14A and the sheath-like contacts 76 of the connector half 14B in substantially the same manner as the first embodiment, without producing any undesirable and imprudent electric current in the signals lines (SSL and USL).

According to the second embodiment, the signal line USL is provided with a NPN-type transistor TR2, which serves as a static-electricity-protector. As shown in FIGS. 12 and 13, a collector of the transistor TR2 is connected to the signal line USL; an emitter of the transistor TR2 is grounded; and a base of the transistor TR2 is connected to an output terminal of a buffer B3 via a resistance R3, with an input terminal of the buffer B3 being connected to the power source circuit 54 via a resistance R4. Note, of course, this is true for the remaining signal lines of the unit side (12). On the other hand, the power control line UCL is extended to the power source circuit 54, and is provided with a by-pass diode DI, which serves as a static-electricity-protector. Note, the power control line UCL is connected to the input terminal of the buffer B3, as shown in FIGS. 12 and 13.

Usually, there is an electrostatic potential difference between a contact pin 82 and a sheath-like contact 76 to be connected to each other, because the contact pin 82 and the sheath-like contact 76 may be electrostatically and individually charged. Thus, when the contact pin 82 and the sheath-like contact 76, exhibiting differing electrostatic potentials, are connected to each other, the electrostatic potential difference therebetween produces an electric current. Consequently, the production of the electric current may result in malfunction of the electronic endoscope and in damage of electronic devices included in the electronic endoscope, and thus it is necessary to immediately eliminate the electric current from the electronic endoscope.

In the second embodiment, when the power ON/OFF switch of the video-signal precessing unit 12 is turned ON, a given voltage is applied to the base of the transistor TR2 in accordance with resistance values of the resistances R3 and R4, thereby turning ON the transistor TR2. When the connector halves 14A and 14B are connected to each other, the ON-state of the transistor TR2 is maintained until a connection is established between the short contact pin 82S of the power control line SCL and the short sheath-like contact 76S of the power control line UCL. Thus, although an electric current is produced by a connection between the contact pin 82 of the signal line SSL and the sheath-like contact 76 of the signal line USL due to an electrostatic potential difference therebetween, the produced electric current is immediately eliminated from the connected signal lines SSL and USL to the ground via the transistor TR2 which is at the ON-state. Of course, as soon as the connection is established between the short contact pin 82S and the short sheath-like contact 76S, the base of the transistor TR2 is grounded so that the ON-state of the transistor TR2 is changed into an OFF-state.

Also, although an electric current is produced by the connection between the short contact pin 82S and the short sheath-like contact 76S due to an electrostatic potential difference therebetween, the produced electric current is immediately eliminated from the connected power control lines SCL and UCL to the power source circuit 54 via the by-pass diode DI.

In the second embodiment, the interface circuit 32 is manufactured as an integrated circuit board in which the transistor TR2, incorporated in each signal line USL, can be formed as one of the electronic elements included in the integrated circuit board. Thus, a cost for the transistors TR2 for all the signal lines USL is very low. On the other hand, the by-pass diode DI, which is relatively costly, is incorporated in only the power control line UCL. Accordingly, it is possible to provide the connection system per se at a low cost.

Further, in the second embodiment, a light-emitting diode LE is provided in the interface circuit 32, and is used to indicate whether the connector halves 14A and 14B are properly connected to each other. Note, the light-emitting diode LE may be provided at a suitable location on the housing wall of the video-signal processing unit 12.

As shown in FIGS. 12 and 13, the light-emitting diode LE is associated with an NPN-type transistor TR3 and a resistance R5. Namely, the light-emitting diode LE is connected, at one end thereof, to the power line UPL via a resistance R5, and is connected, at the other end, to a collector of the transistor TR3. An emitter of the transistor TR3 is connected to the ground line UGL, and a base of the transistor TR3 is connected to an output terminal of an inverter IN via a resistance R6, with an input terminal of the inverter IN being connected to the output terminal of the buffer B3.

In the condition in which the connector halves 14A and 14B are not connected to each other, and when the power ON/OFF switch of the video-signal processing unit 12 is turned ON, an output voltage level of the buffer B3 is high. However, a voltage level, applied to the base of the transistor TR3, is low due to the existence of the inverter IN, so that the transistor TR3 is at an OFF-state, thereby not lighting the light-emitting diode LE. When the connector halves 14A and 14B are connected to each other, the OFF-state of the transistor TR3 is maintained until a connection is established between the short connector pin 82S and the short sheath-like contact 76S.

As soon as the connection is established between the short connector pin 82S and the short sheath-like contact 76S, the input terminal of the buffer B3 is grounded so that the output voltage level of inverter IN is changed from the low level to a high level, whereby the voltage level, applied to the base of the transistor TR3, is changed the low level to a high level, i.e. the OFF-state of the transistor TR3 is changed into an ON-state, thereby lighting the light-emitting diode LE. Of course, by lighting the light-emitting diode LE, it is indicated that the proper connection has been completed between the connector halves 14A and 14B.

Furthermore, in the second embodiment, the output terminal of the inverter IN is connected to the system control circuit 28, which retrieves an output voltage level from the inverter IN as a connection-determination (C/D) signal. Of course, when a level of the C/D signal is low, it indicates that a connection is not yet established between the connector halves 14A and 14B, and, when the C/D signal is changed from the low level to a high level, it indicates that the connector halves 14A and 14B have been properly and completely connected to each other.

Figure 14:
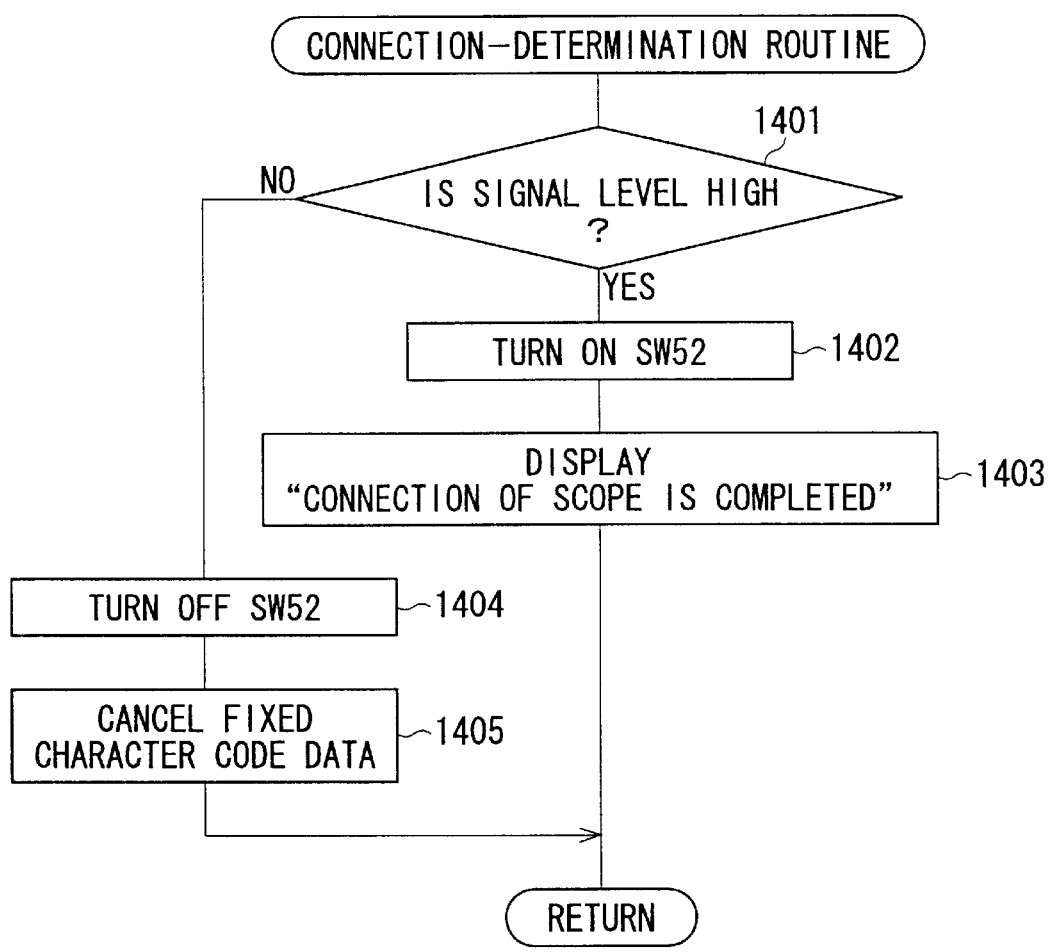
FIG. 14 is a flowchart of a connection-determination routine executed by a system control circuit provided in the video-signal processing circuit.

FIG. 14 shows a flowchart of a connection-determination routine executed by the system control circuit 28. This connection-determination routine is constituted as a time-interruption routine which is repeatedly executed at regular intervals of, for example, 20 ms, and the execution of the routine is started by turning ON the power ON/OFF switch of the video-signal processing unit 12.

Note, when the power ON/OFF switch of the video-signal processing unit 12 is turned ON, the switch circuit 52 is at an OFF-state, and thus a screen of the TV monitor 50 is at an inactive state.

At step 1401, it is determined whether a level of the connection-determination (C/D) signal is high. If the level of the C/D signal is high, i.e. if it is confirmed that the connector halves 14A and 14B have been properly and completely connected to each other, the control proceeds to step 1402, in which the switch circuit 52 is turned ON. Then, at step 1403, a message "CONNECTION OF SCOPE IS COMPLETED" is displayed on a screen of the TV monitor 52. Namely, the fixed character code data corresponding to the message "CONNECTION OF SCOPE IS COMPLETED" is read from the ROM of the system control circuit 28, and is then written in the video RAM of the character generator 44, whereby the display of the message "CONNECTION OF SCOPE IS COMPLETED" is performed on the screen of the TV monitor 50.

After the flexible scope 10 is once connected to the video-signal processing unit, and subsequently the flexible scope 10 is disconnected therefrom, the C/D signal is changed from the high level to the low level. Thus, the control proceeds from step 1401 to step 1404, in which the switch circuit 52 is turned OFF, whereby the feeding of the video-signal from the video-process circuit 38 to the TV monitor 50 is stopped. Then, step 1405, the fixed character code data, corresponding to the message "CONNECTION OF SCOPE IS COMPLETED", is canceled from the video RAM of the character generator 44.

Of course, when the power ON/OFF switch of the video-signal processing unit 12 is initially turned ON, and when the connector halves 14A and 14B are not connected to each other, the control proceeds from step 1401 to step 1404, in which the OFF-state of the switch circuit 52 is maintained, i.e. the inactive state of the screen of the TV monitor 50 is maintained.

Immediately following the connection being established between the connector halves 14A and 14B, although a state of the screen of the TV monitor 50 has been changed from the inactive state to an active state, there may occur a case in which an image is not clearly and stably displayed on the screen of the TV monitor 50. In this case, it cannot be confirmed by a user whether the unclearly displayed image is derived from an incomplete connection between the connector halves 14A and 14B. However, according to the second embodiment, due to the displayed message "CONNECTION OF SCOPE IS COMPLETED", it is possible to easily confirm whether the connection is properly and completely established between the connector halves 14A and 14B.

Also, if the switch circuit 52 is not interposed between the video-process circuit 38 and the TV monitor 50, the screen of the TV monitor 50 becomes active by turning ON the power ON/OFF switch of the video-signal processing unit 12. In this case, no image will be displayed on the active screen of the TV monitor 50 until the connection is properly and completely established between the connector halves 14A and 14B, and the active state of the screen, displaying no image, is redundant.

However, according to the second embodiment, it is possible to maintain the inactive state of the TV monitor 50 until the connection is properly and completely established between the connector halves 14A and 14B due to the switch circuit 52 being interposed between the video-process circuit 38 and the TV monitor 50.

Finally, it will be understood by those skilled in the art that the foregoing description is of preferred embodiments of the connection system, and that various changes and modifications may be made to the present invention without departing from the spirit and scope thereof.

The present disclosure relates to subject matters contained in Japanese Patent Applications No. 10-254987 (filed on Sep. 9, 1998) and No. 10-255024 (filed on Sep. 9, 1998) which is expressly incorporated herein, by reference, in their entireties.

What is claimed is:

1. A connection system for establishing a detachable connection between a scope and a video-signal processing unit which form an electronic endoscope, said scope having a solid-state image sensor to produce image-pixel signals, said video-signal processing unit having a processor for processing said image-pixel signals to produce a video signal, said scope including a first power line, a first group of signal lines and a first ground line which are utilized to feed said image-pixel signals to said unit, said unit including a second power line, a second group of signal lines and a second ground line which are utilized to receive said image-pixel signals from said scope, said connection system comprising:

a connector that includes a first connector half provided on said scope, and a second connector half provided on said unit, said first power line, first group of signal lines and first ground line being connected to said second power line, second group of signal lines and second ground line, respectively, by establishing a connection between said first and second connector halves;

a power switch element provided in one of said first and second power lines; and a power controller that changes an OFF-state of said power switch element to an ON-state after the respective connections are completely established between said first power line, first group of signal lines and first ground line and said second power line, second group of signal lines and second ground line.

2. A connection system as set forth in claim 1, wherein said power controller comprises a first power control line included in said scope, and a second power control line included in said unit; a connection between said first and second power control lines is established after the respective connections are completely established between said first power line, first group of signal lines and first ground line and said second power line, second group of signal lines and second ground line; and the change of the OFF-state of said power switch element to the ON-state is performed by said power controller when the connection is established between said first and second power control lines.

3. A connection system as set forth in claim 1, wherein said power switch element comprises a transistor which is arranged so as to be turned ON by the establishment of the connection between said first and second power control lines.

4. A connection system as set forth in claim 1, wherein said power switch element is provided in said second power line.

5. A connection system as set forth in claim 4, further comprising a switch circuit that controls an output of said video signal from said unit, an OFF-state of said switch circuit being changed to an ON-state when the change of the OFF-state of said power switch element to the ON-state is performed by said power controller, whereby the output of said video signal from said unit is enabled.

6. A connection system as set forth in claim 5, further comprising:

a monitor that reproduces an image on the basis of said output of said video signal from said unit; and a character-display-controller that displays a message on said monitor announcing the establishment of the complete connections between said first power line, first group of signal lines and first ground line and said second power line, second group of signal lines and second ground line when the change of the OFF-state of said power switch element to the ON-state is performed by said power controller.

7. A connection system as set forth in claim 5, wherein said power controller comprises a first power control line included in said scope, and a second power control line included in said unit; a connection between said first and second power control lines being established after the respective connections are completely established between said first power line, first group of signal lines and first ground line and said second power line, second group of signal lines and second ground line; and the change of the OFF-state of said power switch element to the ON-state and the change of the OFF-state of said switch circuit to the ON-state are performed by said power controller when the connection is established between said first and second power control lines.

8. A connection system as set forth in claim 5, wherein said power switch element comprises a transistor which is arranged so as to be turned ON by the establishment of the connection between said first and second power control lines.

9. A connection system as set forth in claim 4, further comprising an indicator that indicates the establishment of the complete connections between said first power line, first group of signal lines and first ground line and said second power line, second group of signal lines and second ground line when the change of the OFF-state of said power switch element to the ON-state is performed by said power controller.

10. A connection system as set forth in claim 9, wherein said indicator comprises a light-emitting diode which is arranged so as to be lit when the change of the OFF-state of said power switch element to the ON-state is performed by said power controller.

11. A connection system as set forth in claim 9, wherein said power controller comprises a first power control line included in said scope, and a second power control line included in said unit; a connection between said first and second power control lines is established after the respective connections are completely established between said first power line, first group of signal lines and first ground line and said second power line, second group of signal lines and second ground line; and the change of the OFF-state of said power switch element to the ON-state is performed by said power controller when the connection is established between said first and second power control lines.

12. A connection system as set forth in claim 9, wherein said power switch element comprises a transistor which is arranged so as to be turned ON by the establishment of the connection between said first and second power control lines.

13. A connection system for establishing a detachable connection between a scope and a video-signal processing unit which form an electronic endoscope, said scope having a solid-state image sensor to produce image-pixel signals, said unit having a processor for processing said image-pixel signals to produce a video signal, said scope including a first power line, a first group of signal lines and a first ground line which are utilized to feed said image-pixel signals to said unit, said unit including a second power line, a second group of signal lines and a second ground line which are utilized to receive said image-pixel signals from said scope, said connection system comprising:

a connector that includes a first connector half provided on said scope, and a second connector half provided on said unit, said first power line, first group of signal lines and first ground line being connected to said second power line, second group of signal lines and second ground line, respectively, by establishing a connection between said first and second connector halves;

a power switch element provided in said second power lines;

a power controller that changes an OFF-state of said power switch element to an ON-state after the respective connections are completely established between said first power line, first group of signal lines and first ground line and said second power line, second group of signal lines and second ground line; and a transistor provided in each of the signal lines included in said second group, said transistor usually being in an ON-state such that the corresponding signal line is grounded, whereby said transistor serves as a static-electricity-protector for the corresponding signal line, the ON-state of said transistor being changed to an OFF-state when the change of the OFF-state of said power switch element to the ON-state is performed by said power controller.

14. A connection system as set forth in claim 13, wherein said power controller comprises a first power control line included in said scope, and a second power control line included in said unit; a connection between said first and second power control lines is established after the respective connections are completely established between said first power line, first group of signal lines and first ground line and said second power line, second group of signal lines and second ground line; and the change of the OFF-state of said power switch element to the ON-state and the change of the ON-state of said transistor to the OFF-state are performed by said power controller when the connection is established between said first and second power control lines.

15. A connection system as set forth in claim 14, further comprising a by-pass diode, which serves as a static-electricity-protector, provided in said second power control line.

16. A connection system as set forth in claim 13, wherein said power switch element comprises a transistor which is arranged so as to be turned ON by the establishment of the connection between said first and second power control lines.

* * * * *